United States Patent
Kepner et al.

(10) Patent No.: US 8,394,420 B2
(45) Date of Patent: Mar. 12, 2013

(54) SUBSTRATES COMPRISING ANTI-MICROBIAL COMPOSITIONS AND METHODS OF MAKING AND USING THE SAME

(75) Inventors: Bryan Kepner, Lancaster, PA (US); Eric Mintz, Roswell, GA (US)

(73) Assignee: K2 Concepts, Inc., Lancaster, PA (US)

( * ) Notice: Subject to any disclaimer, the term of this patent is extended or adjusted under 35 U.S.C. 154(b) by 619 days.

(21) Appl. No.: 12/206,806

(22) Filed: Sep. 9, 2008

(65) Prior Publication Data

US 2009/0001012 A1    Jan. 1, 2009

Related U.S. Application Data

(63) Continuation-in-part of application No. 11/266,562, filed on Nov. 3, 2005, now Pat. No. 7,422,759.

(51) Int. Cl.
 *A01N 59/16* (2006.01)
(52) U.S. Cl. ......................... 424/617; 424/618; 68/17 R
(58) Field of Classification Search .................. 424/617, 424/618; 68/17
 See application file for complete search history.

(56) References Cited

U.S. PATENT DOCUMENTS

| | | | |
|---|---|---|---|
| 3,432,428 A * | 3/1969 | Wirth et al. | 210/668 |
| 3,778,226 A | 12/1973 | Kissa | |
| 3,872,013 A * | 3/1975 | Nishino et al. | 210/317 |
| 4,608,247 A * | 8/1986 | Heinig, Jr. | 424/421 |
| 4,692,314 A | 9/1987 | Etani | |
| 5,527,547 A | 6/1996 | Hight et al. | |
| 5,768,917 A | 6/1998 | Freida | |
| 6,032,495 A | 3/2000 | Leu | |
| 6,267,887 B1 | 7/2001 | Hughes et al. | |
| 6,303,039 B1 | 10/2001 | Back et al. | |
| 6,383,273 B1 | 5/2002 | Kepner et al. | |
| 6,716,808 B1 | 4/2004 | Pancheri et al. | |
| 6,726,936 B1 | 4/2004 | Asano et al. | |
| 7,422,759 B2 * | 9/2008 | Kepner et al. | 424/618 |
| 2003/0022793 A1 | 1/2003 | Ring et al. | |
| 2004/0101572 A1 * | 5/2004 | Kepner et al. | 424/617 |
| 2004/0217326 A1 * | 11/2004 | Souter et al. | 252/179 |

FOREIGN PATENT DOCUMENTS

| | | |
|---|---|---|
| EP | 0 883 990 | 12/1998 |
| GB | 2324727 | 11/1998 |
| WO | WO03/076341 | 9/2003 |

OTHER PUBLICATIONS

SILIPHOS Material Safety Data Sheet, manufacturer—Guilini Chemie Gmbh Co.

* cited by examiner

*Primary Examiner* — Ali Soroush (74) *Attorney, Agent, or Firm* — Withers & Keys, LLC (57) ABSTRACT

Anti-microbial compositions and devices comprising anti-microbial compositions are disclosed. Methods of making and using anti-microbial compositions and devices are also disclosed.

20 Claims, 3 Drawing Sheets

FIG.4

SUBSTRATES COMPRISING ANTI-MICROBIAL COMPOSITIONS AND METHODS OF MAKING AND USING THE SAME

CROSS-REFERENCE TO RELATED APPLICATIONS

This patent application is a continuation-in-part (CIP) patent application of U.S. patent application Ser. No. 11/266,562 filed on Nov. 3, 2005, now U.S. Pat. No. 7,422,759, and claims the benefit of priority to U.S. patent application Ser. No. 11/266,562 filed on Nov. 3, 2005, the subject matter of each of which is hereby incorporated by reference in its entirety.

FIELD OF THE INVENTION

The present invention relates generally to anti-microbial compositions and devices comprising anti-microbial compositions. The anti-microbial compositions may be used to reduce microbes, control bacteria growth, and/or prevent scale deposits in fluid environments such as bodies of water and air. The present invention further relates to methods of making and using anti-microbial compositions and devices containing the same.

BACKGROUND OF THE INVENTION

Room humidifiers, such as portable mist-type humidifiers, and other containers housing a body of water are susceptible to bacteria and fungi growth within their water reservoirs. This bacteria and fungi can be transmitted into the air though the "misting" or atomization of water by the humidifier. This can cause significant health concerns for children, elderly, or anyone who has a weakened immune system.

Standing bodies of water such as those found in humidifiers are subject to contamination by a broad spectrum of microorganisms. In addition, many of the bacteria form biofilms and are therefore more difficult to control. Therefore, a product to control bacterial growth must be effective against a broad spectrum of microorganism, and must be able to function under a variety of water conditions.

Traditionally, oligodynamic metals, phosphates, and chlorination chemicals have been deployed into water by the use of large and sophisticated water treatment systems. These systems require that the oligodynamic, phosphates, and chlorine-based materials be contained in a separate filter-housing vessel. The water to be treated is then required to be pumped under pressure through this filter housing to bring the water in contact with the oligodynamic/phosphoric/chlorination materials. Under this scenario, elaborate filter vessels and pumps are required to treat the water. Such a system is not a viable or economical alternative for many smaller applications such as a room humidifier. Alternatively, technologies such as UV (ultraviolet) light and electrolysis have also been utilized for bacteria control in water, but both require complex electronic systems to operate effectively.

In addition, a variety of air filtration systems are known. These air filtration systems attempt to remove one or more contaminants (e.g., smoke, odors, etc.) from air. Efforts continue to provide devices having the ability to effectively remove contaminants from air.

There is a need in the art for an easily administered anti-microbial composition and/or device containing the same that provides one or more of the following features: prevents or slows bacteria growth in a fluid (e.g., water or air), the formation of scale deposits, removes bacteria from a fluid (e.g., water or air), removes biofilm from a surface of a container of water, controls the reoccurrence of bacteria growth on a surface of a container of water and in the water within the container, and prevents the formation of scale deposits in containers of standing water such as those in humidifiers and vaporizers.

SUMMARY OF THE INVENTION

The present invention is directed to anti-microbial compositions, substrates having an anti-microbial composition thereon, and devices containing an anti-microbial composition. Each of the anti-microbial compositions, substrates having an anti-microbial composition thereon, and devices containing an anti-microbial composition comprises at least one anti-microbial component on a support material. As described below, the anti-microbial compositions, substrates, and devices may further comprise a number of additional components in order to provide one or more properties to the composition, substrate or device. The disclosed anti-microbial compositions, substrates and devices may be used to treat a variety of fluid environments including bodies of water and air.

Accordingly, the present invention is directed to fluid treatment devices. In one exemplary embodiment of the present invention, the fluid treatment device is designed to control microbial growth in water. In this embodiment, the fluid treatment device is desirably porous so as to allow water migration through the walls of the fluid treatment device to come into contact with fluid treatment media contained within or on the device. The fluid treatment device can be easily utilized by simply dropping the fluid treatment device into a body of water to be treated. As water contacts the fluid treatment media, anti-microbial components and optionally scale inhibitors are released into the water at levels that effectively control the bacteria growth in the water, as well as optionally control scale deposition on the surfaces of the container surrounding the water. The fluid treatment devices of the present invention enable easy application and effective control of bacteria growth and scale buildup without elaborate equipment.

In another exemplary embodiment of the present invention, the fluid treatment device for controlling microbial growth in water comprises (I) a flow-through housing having a housing wall structure, a housing volume surrounded by the housing wall structure, and one or more openings within the housing wall structure; and (II) fluid treatment media occupying at least a portion of the housing volume within the flow-through housing, wherein the fluid treatment media comprises (a) an anti-microbial component on (b) a support material; and (c) at least one of (i) a bifunctional ligand, (ii) a scale inhibitor and (iii) a disinfectant/biofilm removal material; wherein the fluid treatment media has a size that prevents the fluid treatment media from escaping the one or more openings within the housing wall structure.

In a further exemplary embodiment of the present invention, the fluid treatment device for controlling microbial growth in water comprises (I) a flow-through housing having a housing wall structure, a housing volume surrounded by the housing wall structure, and one or more openings within the housing wall structure; wherein the housing wall structure of the flow-through housing comprises (i) an upper half, (ii) a lower half connected to the upper half, and (iii) a filling cap connected to the upper half or the lower half; wherein the one or more openings are positioned within the upper half, the lower half, or both; and (II) fluid treatment media occupying at least a portion of the housing volume within the flow-through housing, wherein the fluid treatment media comprises (a) an anti-microbial component on (b) a support material; wherein the fluid treatment media has a size that prevents the fluid treatment media from escaping the one or more openings within the housing wall structure. In one desired embodiment, the flow-through housing has a spherical shape formed from (i) the upper half, (ii) the lower half, and (iii) the filling cap. The fluid treatment media may further comprise at least one of (i) a bifunctional ligand, (ii) a scale inhibitor and (iii) a disinfectant/biofilm removal material.

In yet a further exemplary embodiment of the present invention, the fluid treatment device for controlling microbial growth in water comprises (I) a flow-through housing having a housing wall structure, a housing volume surrounded by the housing wall structure, and one or more openings within the housing wall structure; wherein the housing wall structure of the flow-through housing comprises (i) an upper half, (iii) a lower half connected to the upper half, and (iii) a filling cap connected to the upper half or the lower half; wherein the one or more openings are positioned within the upper half, the lower half, or both; and (II) fluid treatment media occupying at least a portion of the housing volume within the flow-through housing, wherein the fluid treatment media comprises (a) an anti-microbial component on (b) a support material, wherein the anti-microbial component comprises a transition metal, a transition metal oxide, or a combination thereof, and (c) at least one of (i) a scale inhibitor comprising an inorganic phosphate, a phosphonate, a polycarboxylate, or a combination thereof, and (ii) a disinfectant/biofilm removal material comprising sodium percarbonate, calcium hypochlorite, potassium monopersulfate, sodium persulfate, or a combination thereof, wherein the fluid treatment media has a size that prevents the fluid treatment media from escaping the one or more openings within the housing wall structure.

In yet a further exemplary embodiment of the present invention, the fluid treatment device is used to control microbial growth in air. In this embodiment, the fluid treatment device comprises (I) a substrate, and (II) fluid treatment media on and/or in the substrate, wherein the fluid treatment media comprises (a) an anti-microbial component on (b) a support material. In this embodiment, the fluid treatment device may be used to remove one or more contaminants from air by allowing air to contact a portion of the fluid treatment device and/or flow through a portion of the fluid treatment device.

The present invention is also directed to methods of making fluid treatment devices. In one exemplary embodiment of the present invention, the method of making a fluid treatment device comprises the step of (i) forming three molded parts comprising an upper half, a lower half, and a filling cap; (ii) connecting the upper half to the lower half to form a flow-through housing having a housing wall structure, a housing volume surrounded by the housing wall structure, one or more openings within the housing wall structure, and a filling cap opening; (iii) forming a fluid treatment media comprising an anti-microbial component on a support material; (iv) introducing the fluid treatment media into the filling cap opening to fill at least a portion of the housing volume with fluid treatment media; and (v) connecting the filling cap to the flow-through housing to cover the filling cap opening. In one desired embodiment, the three molded parts connect to one another to form a spherical fluid treatment device.

In a further exemplary embodiment of the present invention, the method of making a fluid treatment device comprises (i) providing a substrate; (ii) forming a fluid treatment media comprising an anti-microbial component on a support material; and (iii) applying the fluid treatment media onto the substrate so as to coat and/or impregnate the substrate with fluid treatment media. The step of applying the fluid treatment media onto the substrate may comprise any conventional coating process such as a dip coating or spray coating process step.

The present invention is further directed to methods of using fluid treatment devices to control the growth of microbes in a body of water or air. In one exemplary embodiment of the present invention, the method comprises a method of treating a body of water in a container, wherein the method comprises the step of inputting a fluid treatment device into the body of water within the container, wherein the fluid treatment device comprises (I) a flow-through housing having a housing wall structure, a housing volume surrounded by the housing wall structure, and one or more openings within the housing wall structure; and (ii) fluid treatment media occupying at least a portion of the housing volume within the flow-through housing, wherein the fluid treatment media comprises (a) an anti-microbial component on (b) a support material, and (c) at least one of (i) a scale inhibitor and (ii) a disinfectant/biofilm removal material; wherein the fluid treatment media has a size that prevents the fluid treatment media from escaping the one or more openings within the housing wall structure.

In a further exemplary embodiment, the fluid treatment devices of the present invention may be used to extend the life and/or vitality of a plant, cut flowers, fruits or vegetables. In one exemplary embodiment, the present invention is directed to a method of extending the life and/or vitality of a plant, cut flowers, fruits or vegetables, wherein the method comprises the steps of (a) inputting at least a portion of a plant into a body of water within a container; (b) inputting a fluid treatment device into the body of water, said fluid treatment device comprising (i) a flow-through housing having a housing wall structure, a housing volume surrounded by the housing wall structure, and one or more openings within the housing wall structure, and (ii) fluid treatment media occupying at least a portion of the housing volume within the flow-through housing, the fluid treatment media comprising an anti-microbial component on a support material; wherein the fluid treatment media has a size that prevents the fluid treatment media from escaping the one or more openings within the housing wall structure. In this embodiment, the fluid treatment devices of the present invention may be used to extend the life or vitality of a variety of plants including cut flowers, such as roses.

These and other features and advantages of the present invention will become apparent after a review of the following detailed description of the disclosed embodiments and the appended claims.

BRIEF DESCRIPTION OF THE FIGURES

The present invention is further described with reference to the appended figures, wherein.

DETAILED DESCRIPTION OF THE INVENTION

The present invention is directed to devices suitable for treating fluids such as bodies of water and air. For example, the devices may be used to prevent the growth of microbes in a body of water and/or scale deposits along a container surface housing the body of water. The present invention is further directed to methods of making, as well as methods of using the devices to treat a fluid such as a body of water.

The fluid treatment devices of the present invention may comprise a number of components. A description of individual components and combinations of individual components is provided below.

I. Device Components

The fluid treatment devices of the present invention may comprise one or more of the following components.

A. Fluid Treatment Media

The devices of the present invention comprise a fluid (e.g., water or air) treatment media containing one or more of the following components.

1. Rigid Support Material

The fluid treatment media suitable for delivering one or more active ingredients to a fluid (e.g., a body of water) comprises a rigid support material. The support material may be porous or nonporous. Typically, the support material is non-bioactive and water-insoluble. In one exemplary embodiment of the present invention, the support material is an inert, nonbioactive, and water-insoluble support material. In a further exemplary embodiment of the present invention, the support is an adsorbent material. In this further embodiment, the adsorbent property of the support material is utilized to control the level of metal and/or scaling agent in a given fluid (e.g., water) within the vicinity of the support material.

Support materials suitable for use in the present invention include, but are not limited to, activated carbon, metal oxides, polymeric materials, and combinations thereof. Any known metal oxide may be used as the support material in the present invention. Examples of suitable metal oxides include, but are not limited to, oxide complexes, such as transition metal oxides, lanthanide oxides, as well as oxides of Group IIA (Mg, Ca, Sr, Ba), Group IIIA (B, Al, Ga, In, Ti), Group IVA (Si, Ge, Sn, Pb), and Group VA (As, Sb, Bi). In one exemplary embodiment, the metal oxide comprises an oxide of aluminum, titanium, tin, lanthanum, copper, vanadium, silicon, manganese, nickel, iron, zinc, zirconium, magnesium, thorium, or a combination thereof. For example, the metal oxide may comprise $Al_2O_3$, $TiO_2$, $CuO$, $Cu_2O$, $V_2O_5$, $SiO_2$, $MnO_2$, $Mn_2O_3$, $Mn_3O_4$, $ZnO$, $MgO$, $ThO_2$, $Fe_2O_3$, $Fe_3O_4$, or zeolite. In one desired embodiment, the support material is aluminum oxide, silicon dioxide, or an oxide of magnesium. When the support material is an inorganic material, the support material desirably comprises alumina.

In a further embodiment, the support material comprises a mixture of oxide particles comprising at least two separate oxides such as combinations of two or more oxides of aluminum, titanium, copper, vanadium, silicon, manganese, iron, zinc, zirconium, magnesium, or thorium. For example, the mixture of oxide particles may comprise aluminum oxide, titanium dioxide, copper oxide, vanadium pentoxide, silicon dioxide, manganese dioxide, iron oxide, zinc oxide, and/or zeolite. In one embodiment, the support comprises a mixture of aluminum oxide, silicon dioxide, and/or an oxide of magnesium.

Other useful support materials include polymeric or plastic supports. Suitable polymeric or plastic support materials include, but are not limited to, polyethers, such as polyethylene oxide; thermoplastic polymers, such as polyethylene, polypropylene, polystyrene, polyvinyl chloride, polyvinylidene chloride, polyamides, polyesters such as polyethylene terephthalate, polyvinyl alcohol, polycarbonates, polyacetals, ABS resins, acrylic resins, fluorine-contained resins, polyurethane elastomers, polyester elastomers; thermoset polymers, such as phenolic resins, urea resins, and urethane resins. When the support material is a polymeric material, the support material is desirably polypropylene or polyethylene terephthalate.

The size and shape of the support material may vary depending on a number of factors such as the particular application (e.g., a humidifier), the fluid to be treated (e.g., air or water), a volume of fluid to be treated, the desired concentration of active ingredients in the fluid, the configuration of the device (e.g., a flow-through device or a treated substrate), etc. Typically, the support material is in the form of particles or beads having an overall average particle size of up to about 2.54 centimeters (cm) (1.0 inch). As used herein, the term "overall average particle size" refers to the average length of the largest dimension of the particle or bead. For example, in the case of a spherical particle or bead, the overall average particle size is the average diameter of the spherical particle or bead. In one exemplary embodiment of the present invention, the support material is in the form of particles or beads having an overall average particle size ranging from about 5.0 microns (μm) (0.0002 inches) to about 12.7 mm (0.5 inches) in diameter, desirably, 0.03 mm (0.001 inches) to about 12.7 mm (0.5 inches) in diameter, more desirably from about 0.8 mm (0.031 inches) to about 6.4 mm (0.25 inches) in diameter, and even more desirably from about 1.0 mm (0.039 inches) to about 4.8 mm (0.19 inches) in diameter.

The support material may have a regular or irregular shape. For example, the support material may have a regular shape such as a spherical, rectangular or pyramidal shape. In other embodiments, the support material may have an irregular shape such as a rock or pebble-like shape. In one desired embodiment of the present invention, the support material is in the form of spherical beads.

As discussed above, the support material may be porous or nonporous. Suitable porous support materials include, but are not limited to, polymeric foam beads formed from one or more of the above-mentioned polymers. Further, the support material may have a surface area that varies depending on the desired material. For example, the support material may have a relatively high surface area, e.g., from about 200 to about 300 $m^2/g$, or a relatively low surface area, e.g., from about 50 to about 100 $m^2/g$.

2. Anti-Microbial Material

The water treatment media further comprises one or more anti-microbial components. The one or more anti-microbial components are positioned within and/or on an outer surface of the rigid support material. Suitable anti-microbial components include, but are not limited to, transition metals, transition metal oxides, transition metal salts, transition metal compounds, or a combination thereof. The anti-microbial components typically are on the above-described rigid support material. The anti-microbial components can be in the form of solid particles or layers of one or more anti-microbial components on the support material. Where layered anti-microbial components are employed, the components may be produced by methods such as plasma spraying, liquid spraying, sputtering, incipient wetness, gas phase impregnation, electroless plating, precipitation, and absorption.

The anti-microbial components are desirably selected from transition metals, transition metal oxides, insoluble or slightly soluble transition metal salts or compounds, or mixtures thereof from Groups 3-12 of the Periodic Table. Examples of transition metals suitable for use in the present invention include, but are not limited to, Sc, Sn (As used herein, "Sn" includes all oxidation states of Sn even if a given oxidation state is not technically a transition metal.), Ti, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, Rf, Db, Sg, Bh, Hs, Mt, Uun, Uuu, Uub, and combinations thereof. In one desired embodiment of the present invention, the anti-microbial component comprises Ag, Cu, Zn, or combinations thereof with Ag, Cu or combinations thereof being even more desirable. Examples of transition metal oxides suitable for use in the present invention include, but are not limited to, oxides of Ag, Cu, Zn and Sn, desirably, oxides of Ag, Cu and Zn, and more desirably, oxides of Ag and Cu. In addition, alloys of transition metals such as CuZn manufactured by KDF Fluid Treatment, Inc. (Detroit, Mich.) may be used as the anti-microbial component in the present invention.

Examples of insoluble or slightly soluble transition metal salts suitable for use in the present invention include, but are not limited to, AgCl, AgBr, AgI, $Ag_2S$, $Ag_3PO_4$, $NaAg_2PO_4$, CuS, and $NaCuPO_4$. Other examples of silver compounds include, but are not limited to, $AgNO_3$, $Ag_2CO_3$, AgOAc, $Ag_2SO_4$, $Ag_2O$, $[Ag(NH_3)_2]Cl$, $[Ag(NH_3)_2]Br$, $[Ag(NH_3)_2]I$, $[Ag(NH_3)_2]NO_3$, $[Ag(NH_3)_2]_2SO_4$, silver acetoacetate, a silver benzoate, a silver carboxylate, silver amine complexes such as $[Ag(NR_3)_2]X$, where R is an alkyl or aryl group or substituted alkyl or aryl group and X is an anion such as, but not limited to, $Cl^-$, $Br^-$, $I^-$, $OAc^-$, $NO_3^-$ and $SO_4^{2-}$. Examples of copper compounds include, but are not limited to $Cu(NO_3)_2$, $CuCO_3$, $CuSO_4$, $CuCl_2$, $CuBr_2$, $CuI_2$, CuO, $Cu_2O$, CuI, $Cu(OAc)_2$, copper acetoacetate, copper gluconate, a copper benzoate, a copper carboxylate, copper amine complexes such as $[Cu(NR_3)_2]X_2$, where R is an alkyl or aryl group or substituted alkyl or aryl group and X is an anion such as, but not limited to, $Cl^-$, $Br^-$, $I^-$, $OAc^-$, $NO_3^- SO_4^{2-}$.

The transition metals, transition metal oxides or transition metal salts may be employed in a wide range of sizes depending on the specific application. When used as one or more layers on the rigid support material, the transition metals, transition metal oxides or transition metal salts are desirably nanoparticles having an average particle size ranging from about 0.1 nm to about 10,000 nm, more desirably, from about 1 nm to about 1000 nm, and even more desirably, from about 2 nm to about 500 nm diameter. Alternatively, the transition metals, transition metal oxides or metal salts may be bulk material (i.e. larger than nanoparticles). For example, the transition metals, transition metal oxides or metal salts may be supplied in particle sizes up to several millimeters (mm).

When Ag is employed as the anti-microbial component, the device desirably provides solvated silver ions at a concentration of about 1 ppb to about 1000 ppb for control of microbial growth within potable water systems. However, for some applications the levels of solvated Ag ions may be higher as desired.

The anti-microbial components of the fluid treatment media (e.g., the above-described metals, metal oxides, and/or transition metal salts or compounds) may be present in an amount of up to about 15 weight percent (wt %) based on a total weight of the fluid treatment media (i.e., the support material, the anti-microbial components, and any other components). Desirably, the anti-microbial components are present in an amount ranging from about 0.01 wt % to about 15 wt %, more desirably from about 0.1 wt % to about 7.4 wt %, even more desirably from about 0.2 wt % to about 4.8 wt %, and even more desirably from about 0.35 wt % to about 3.5 wt % based on a total weight of the fluid treatment media.

A number of commercially available materials may be used in the present invention as the fluid treatment media. Suitable commercially available materials include, but are not limited to, fluid treatment media designated "MB2001-B" and "MB2002-B," each of which are commercially available from Apyron Technologies, Inc. (Atlanta, Ga.). The MB 2001-B product comprises a plurality of 2-3 mm alumina beads coated with a 2-500 nm thick Ag coating. The MB 2001B product contains 0.7 wt % Ag based on a total weight of Ag and alumina. The MB 2002-B product comprises a plurality of 2-3 mm alumina beads coated with a 2-500 nm thick Cu coating. The MB2002B product contains 4.0 wt % Cu based on a total weight of Cu and alumina. Mixtures of the MB2001-B and MB2002-B products are also useful as a fluid treatment media in the present invention.

Other commercially available materials suitable for use as fluid treatment media include, but are not limited to, products commercially available from K2 Concepts, Inc. (Atlanta, Ga.) under the trade designation AQUASTAT®, such as AQUASTAT® XR (a plurality of 3.2 mm (0.125 inch) alumina beads coated with a 2-500 nm thick Ag coating resulting in about 1.4 wt % Ag on alumina); products commercially available from Sinanen Co., Ltd. (Tokyo, JAPAN) under the trade designation ZEOMIC™ and comprising a silver coating on a zeolite support; products commercially available from Zodiac Pool Care, Inc. (Pompano Beach, Fla.) and comprising silver, copper, and zinc on spherical supports, and silver impregnated carbon available from Barnaby Sutcliff Corporation (Columbus, Ohio).

In one desired embodiment of the present invention, the fluid treatment media comprises a mixture of Ag/Cu, Ag/Zn, Ag/Sn or Ag/Ni. More desirably, the fluid treatment media comprises a mixture of Ag and Cu nanoparticles having an average particle size ranging from about 0.1 nm to about 10,000 nm, more desirably from about 1 nm to about 1000 nm, even more desirably from about 2 nm to about 500 nm. In this desired embodiment, the ratio of Ag to Cu in the mixture may vary from a weight ratio of about 100:1 (Ag:Cu), desirably about 10:1 to about 1:5 (Ag:Cu), more desirably about 1:1 (Ag:Cu).

In another desired embodiment of the present invention, the fluid treatment media comprises a mixture of Ag and Cu nanoparticles on an alumina support material. In this embodiment, the silver nanoparticles have a median size of about 20 nm and the copper nanoparticles have a median size of about 100 nm. Each of the silver nanoparticles and the copper nanoparticles may be present in the mixture in an amount ranging from about 0.2 wt % to about 4.8 wt %, desirably about 0.5 wt % to about 4.5 wt %, more desirably about 0.7 wt % to about 4.0 wt % based on a total weight of the fluid treatment media. In one desired embodiment, the fluid treatment media comprises a 1:1 mixture (i.e., 1:1 weight ratio) of Ag nanoparticle and Cu nanoparticle on an alumina support material.

In a further desired embodiment of the present invention, the fluid treatment media comprises a mixture of silver oxide and copper oxide on a support material, such as an alumina support material. Useful copper oxides include both cuprous oxide and cupric oxide with cuprous oxide being the preferred oxide. The amounts of silver oxide and copper oxide may vary over a wide range. Typically, each of the silver oxide and copper oxide is present in an amount of about 0.1 wt % to about 2.0 wt %, desirably from about 0.5 wt % to about 1.5 wt %, more desirably from about 0.7 wt % to about 1.0 wt % based on a total weight of the fluid treatment media. The purities of silver oxide and copper oxide may vary over a wide range. Typically, the oxides are about 80 wt % to about 99.999 wt % pure, desirably about 90 wt % pure to about 99.99 wt % pure, more desirably about 98 wt % to about 99.99 wt % pure.

In yet a further embodiment of the present invention, the fluid treatment media comprises a mixture of silver and copper metal nanoparticles in combination with nanoparticles of one or more additive metals or metal oxides from Groups 2-13 of the Periodic Table. The additive metals may be Sc, Ti, V, Sn, Cr, Mn, Fe, Co, Ni, Zn, Y, Zr, Nb, Mo, Tc, Ru, Rh, Pd, Cd, Hf, Ta, W, Re, Os, Ir, Pt, Au, Hg, Rf, Db, Sg, Bh, Hs, Mt, Uun, Uuu or Uub. Desirably, the additive metals comprise Zn, Sn, Ni, more desirably Zn and Sn. The additive metal oxides may be oxides such as alumina and silica, as well as oxides of silver, titanium, tin, lanthanum, copper, vanadium, manganese, nickel, iron, zinc, zirconium, magnesium, thorium, or a combination thereof. Desirably, the additive metal oxides are oxides of silver, copper, tin, zinc, or nickel, more desirably silver. The additive metal or metal oxide may be present in an amount ranging from about 0.01 wt % to about 99.9 wt %, desirably from about 0.1 wt % to about 10 wt %, more desirably from about 1.0 wt % to about 5.0 wt % based on a total weight of the mixture (i.e., the coating material). In this embodiment, the combined weight of silver and copper in the mixture is from about 0.1 wt % to about 5.0 wt %, and the weight of additive metal or metal oxide is from about 0.05 wt % to about 5.0 wt % based on a total weight of the fluid treatment media.

3. Scale Inhibitor Material

The fluid treatment media may further comprise one or more scale inhibitors. Like the anti-microbial component, the one or more scale inhibitors may be positioned within and/or on an outer surface of the rigid support material. Suitable scale inhibitors include, but are not limited to, inorganic phosphates, such as hexametaphosphate, orthophosphate, or a combination thereof, phosphonates; polycarboxylates; and any combination thereof. The scale inhibitors are typically combined with the above-described rigid support material with or without one or more anti-microbial components thereon.

The scale inhibitors are typically present as particulate material in addition with the above-described rigid support material. The scale inhibitors may be in the form of particles or beads having a particle size and particle shape similar to the above-described rigid support materials. Desirably, the scale inhibitors and the anti-microbial components are present as a physical mixture of (i) scale inhibitor particles or beads, and (ii) anti-microbial components on the above-described rigid support material.

When present, the scale inhibitors may be present in an amount of up to about 99 weight percent (wt %) based on a total weight of the fluid treatment media (i.e., the support material, any anti-microbial components, any scale inhibitors, and any other components). Desirably, the scale inhibitors, when present, are present in an amount ranging from about 0.01 wt % to about 50.0 wt %, more desirably from about 5.0 wt % to about 30.0 wt %, even more desirably from about 8.0 wt % to about 22.0 wt %, and even more desirably about from about 10.0 to about 20.0 wt % based on a total weight of the fluid treatment media.

A number of commercially available scale inhibitors may be used in the present invention. Suitable commercially available scale inhibitors include, but are not limited to, a variety of scale inhibitors commercially available from BK Giulini Chemie Gmbh & Co. (Ludwigshafen, Germany) such as slowly soluble phosphate spheres or pellets sold under the trade designations SILIPHOS® and MIKROPHOS®; inorganic phosphates and combinations of phosphates sold under the trade designations LUPHOS® and ALBAPHOS®; phosphonates and combinations of phosphonates sold under the trade designation AKTIPHOS®; polycarboxylates and combinations thereof sold under the trade designation GILU-FLER®; and organic and inorganic special inhibitors sold under the trade designations KORRODEX® and LABUXAN®. Other commercially available scale inhibitors suitable for use in the present invention include scale inhibitors commercially available from Southeast Filtration and Equipment Systems, Inc. (Canton, Ga.) sold under the trade designations SCALESAFE™ and HYDROBLEND™.

In one desired embodiment of the present invention, the fluid treatment media comprises a physical mixture of (i) 90 wt % AQUASTAT® XR antimicrobial material, and (ii) 10 wt % SILIPHOS® scale inhibitor material, based on a total weight of the fluid treatment media. In another desired embodiment of the present invention, the fluid treatment media comprises a physical mixture of (i) 90 wt % MB2001B antimicrobial material, and (ii) 10 wt % SILIPHOS® scale inhibitor material, based on a total weight of the fluid treatment media.

4. Disinfectant/Biofilm Removal Material

The fluid treatment media may further comprise one or more disinfectant/biofilm removal materials, particularly when the fluid comprises water or an aqueous liquid. Like the anti-microbial component and the optional scale inhibitors, the one or more disinfectant/biofilm removal materials may be positioned within and/or on an outer surface of the rigid support material. Suitable disinfectant/biofilm removal materials include, but are not limited to, inorganic carbonates, such as sodium percarbonate (also known as sodium carbonate peroxyhydrate, sodium carbonate peroxide, and solid hydrogen peroxide) calcium hypochlorite, potassium monopersulfate, sodium persulfate, or a combination thereof. The disinfectant/biofilm removal material is typically combined with the above-described rigid support material with or without one or more anti-microbial components thereon.

The disinfectant/biofilm removal material is typically present as particulate material in addition to the above-described rigid support material. The disinfectant/biofilm removal material may be in the form of a single tablet used in combination with the above-described rigid support material. Alternatively, the disinfectant/biofilm removal material may be in the form of a plurality of particles or beads having a particle size and particle shape similar to the above-described rigid support materials. Desirably, the disinfectant/biofilm removal material and the anti-microbial components are present as a physical mixture of (i) disinfectant/biofilm removal particles or beads, (ii) anti-microbial components on the above-described rigid support material, and optionally (iii) at least one of the above-described scale inhibitors.

When present, the disinfectant/biofilm removal material may be present in an amount of up to about 99 weight percent (wt %) based on a total weight of the fluid treatment media (i.e., the support material, any anti-microbial components, any scale inhibitors, and any other components). Desirably, the disinfectant/biofilm removal material, when present, is present in an amount ranging from about 0.01 wt % to about 50.0 wt %, more desirably from about 5.0 wt % to about 30.0 wt %, even more desirably from about 8.0 wt % to about 22.0 wt %, and even more desirably about from about 5.0 to about 20.0 wt % based on a total weight of the fluid treatment media.

The disinfectant/biofilm removal materials are believed to provide an initial biofilm removal treatment to a given body of water and the container housing the water. The disinfectant/ biofilm removal material disinfects/shock treats the body of water by producing hydrogen peroxide. The hydrogen peroxide reacts with contaminants in the water and/or on a surface of a container or system component that comes into contact with water (e.g., tubing). The hydrogen peroxide is effective in removing biofilm that may have accumulated on container or system component surfaces that have come into contact with water, as well as sanitize the entire system. Once the initial biofilm removal has taken effect, the above-described anti-microbial materials provide continued treatment of the fluid (i.e., water) system, preventing subsequent regrowth of biofilm.

A number of commercially available disinfectant/biofilm removal materials may be used in the present invention. Suitable commercially available disinfectant/biofilm removal materials include, but are not limited to, disinfectant/biofilm removal materials commercially available from A-dec Incorporated (Newberg, Oreg.) such as water soluble sodium percarbonate tablets or pellets sold under the trade designations ICX™, and disinfectant/biofilm removal materials commercially available from Mallinckrodt Baker, Inc. (Phillipsburg, N.J.), such as sodium persulfate.

In one desired embodiment of the present invention, the fluid treatment media comprises a physical mixture of (i) 90 wt % AQUASTAT® XR antimicrobial material, and (ii) 10 wt % ICX™ disinfectant/biofilm removal material, based on a total weight of the fluid treatment media. In another desired embodiment of the present invention, the fluid treatment media comprises a physical mixture of (i) a physical mixture of (i) 80 wt % AQUASTAT® XR antimicrobial material, (ii) 10 wt % SILIPHOS® scale inhibitor material, and (iii) 10 wt % ICX™ disinfectant/biofilm removal material, based on a total weight of the fluid treatment media. In another desired embodiment of the present invention, the fluid treatment media comprises a physical mixture of (i) a physical mixture of (i) 70 wt % AQUASTAT® XR antimicrobial material, (ii) 20 wt % SILIPHOS® scale inhibitor material, and (iii) 10 wt % ICX™ disinfectant/biofilm removal material, based on a total weight of the fluid treatment media.

5. Bifunctional Ligands

In some embodiments of the present invention, the fluid treatment media further comprise one or more bifunctional ligands. The one or more bifunctional ligands may be present on an outer surface of the above-described rigid support material so as to bind one or more of the above-described anti-microbial materials to the rigid support material. Suitable ligands for use in the present invention include any bifunctional ligand that has (i) at least one functional group capable of binding with the anti-microbial material, and (ii) at least one functional group capable of binding with the support material. Functional groups suitable for binding to the anti-microbial material include, but are not limited to, primary, secondary or tertiary amines; primary, secondary or tertiary alcohols; primary, secondary or tertiary carboxylic acids; primary, secondary or tertiary amino acids; primary, secondary or tertiary phosphines; primary, secondary or tertiary thiols; and combinations thereof. Functional groups suitable for binding to the support material include, but are not limited to, primary, secondary or tertiary amines; primary, secondary or tertiary alcohols; primary, secondary or tertiary thiol; sulfanates; and combinations thereof.

Specific bifunctional ligands suitable for use in the present invention include, but are not limited to, $HOCH_2CH_2NH_2$, $HOCH_2CH(OH)CH_2NH_2$, $HOCH_2CH(NH_2)CH_2NH_2$, $HOCH_2CH(OH)CH(OH)CH_2NH_2$, $HOCH_2CH(OH)CH_2COOH$, $NH_2CH_2CH(OH)CH_2COOH$, $HOOCCH_2CH(NH_2)CH_2COOH$, $HOCH_2CH(OH)CH_2COOH$, $HOCH_2CH(NH_2)CH_2COOH$, or a combination thereof.

It is believed that the bifunctional ligand, bound to both the rigid support material and the anti-microbial material, modifies the rate of release of the anti-microbial material into a given fluid environment (e.g., body of water or air). The release of the anti-microbial material kills bioactive agents present in the fluid environment, as well as prevents the growth of new bioactive agents. Additionally, the rigid support/bifunctional ligand system over time can leach out the anti-microbial material. The amount of anti-microbial material released into the fluid environment can vary depending upon the rigid support/bifunctional ligand system and the anti-microbial material selected.

When present, the bifunctional ligands are present in an amount ranging from about 0.1 wt % to about 10 wt %, more desirably from about 0.2 wt % to about 5.0 wt %, and even more desirably from about 0.5 wt % to about 3.0 wt %, based on a total weight of the fluid treatment media (i.e., the support material, any anti-microbial components, any scale inhibitors, and any other components).

In one desired embodiment, the anti-microbial composition comprises a rigid support in the form of alumina or silica; one of more of the above-described ligands attached to the rigid support; and one of more of the above-described anti-microbial materials attached to the ligands or the ligands and the rigid support. In this embodiment, the anti-microbial material is desirably a silver or copper containing anti-microbial material.

B. Flow-Through Housing

The devices of the present invention may further comprise a flow-through housing such as exemplary flow-through housing 10 shown in FIGS. 1-2. The flow-through housing prevents the fluid treatment media from dispersing into a fluid (e.g., a body of water) undergoing treatment while allowing free flow of fluid (e.g., water) through the flow-through housing in order to contact the fluid treatment media contained within the housing.

The flow-through housing may be formed from any inert, water-insoluble material. Suitable materials include, but are not limited to, acrylonitrile butadiene styrene (ABS), polyvinylchloride (PVC), high density polyethylene (HDPE), polypropylene (PP), low density polyethylene (LDPE), polystyrene, high impact polystyrene, nylon, DELRIN®, urethane, vinyl, ultrahigh molecular weight polypropylene (UHMWPP), polyurethane, phenolic resins, PLEXIGLAS®, stainless steel, carbon steel, and aluminum. In one desired embodiment of the present invention, the flow-through housing is formed from polypropylene or nylon.

The flow-through housing may be formed in a variety of shapes and sizes depending on a given application. Suitable shapes include, but are not limited to, a cube, a sphere, an octagonally-shaped sphere, or a hexagonally-shaped cylinder, or any other geometric solid. In one desired embodiment of the present invention, the flow-through housing has a spherical shape and housing configuration as shown in FIGS. 1-2.

The flow-through housing has a size that may vary depending upon a given application and volume of fluid (e.g., water). For applications such as room humidifiers, the flow-through housing typically has a size such that the largest dimension (e.g., diameter, length, width or height) is up to about 15.2 cm (6.0 inches). In some embodiments, the flow-through housing desirably has a size such that the largest dimension ranges from about 1.3 cm (0.5 in) to about 5.1 cm (2.0 in), more desirably, about 2.5 cm (1.0 in). In one exemplary embodiment of the present invention, the flow-through housing has a spherical shape and a diameter of about 33 mm (1.3 in).

Figure 1:
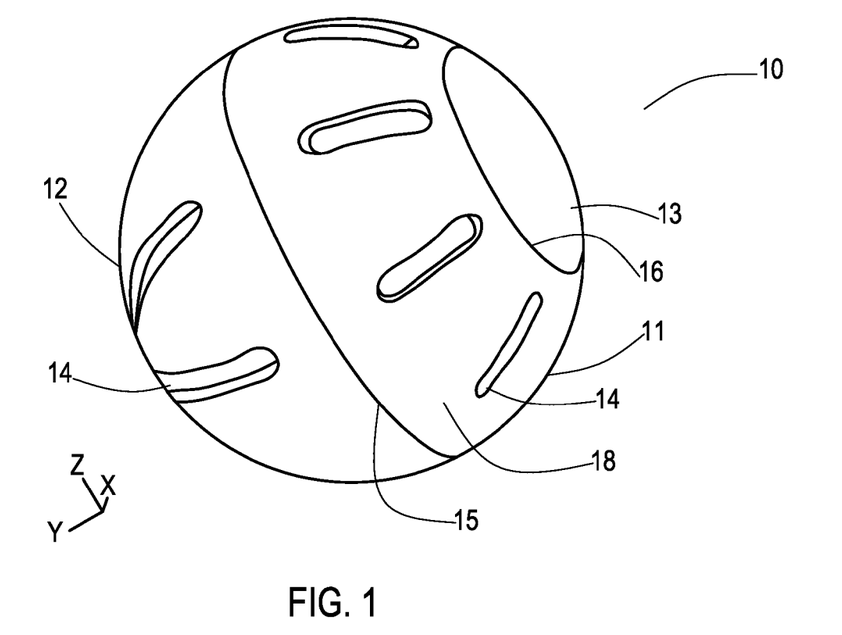
FIG. 1 depicts a perspective view of an exemplary flow-through housing for use in an exemplary device of the present invention.
Figure 2:
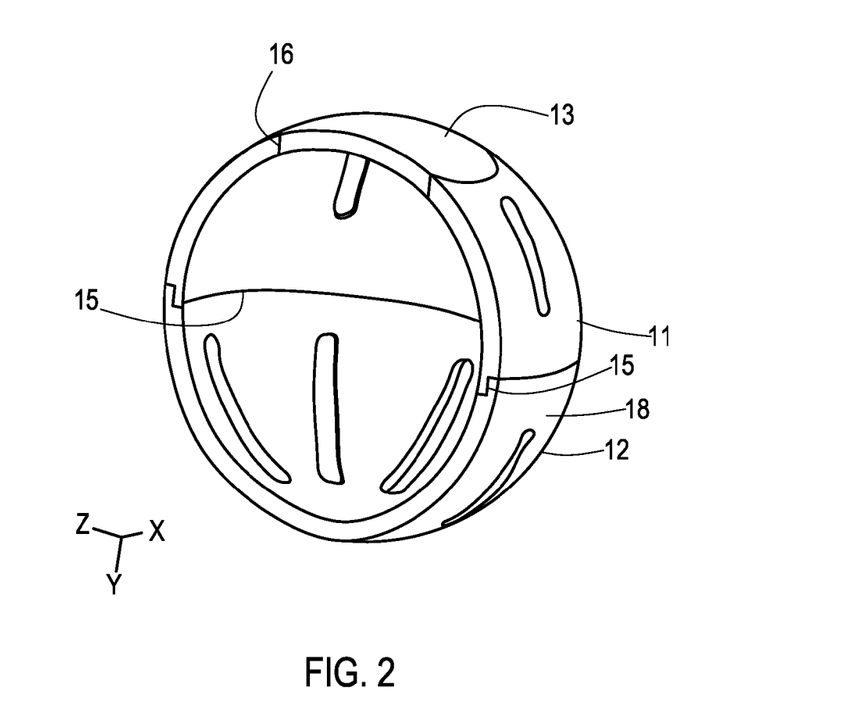
FIG. 2 depicts a cross-sectional view of the exemplary flow-through housing shown in FIG. 1.

In one desired embodiment of the present invention, the flow-through housing has a spherical shape and configuration as shown in FIGS. 1-2. As shown in FIG. 1, exemplary flow-through housing 10 comprises three distinct parts: upper half 11, lower half 12 and filling cap 13. Upper half 11, lower half 12 and filling cap 13 may be assembled with one another to form flow-through housing 10 having numerous openings 14 within outer wall surface 18 of flow-through housing 10. FIG. 2 provides a cross-sectional view of flow-through housing 10. As shown in FIG. 2, upper half 11 and lower half 12 are connected to one another along body seam 15. Filling cap 13 is attached to upper half 11 along cap seam 16.

Upper half 11, lower half 12 and filling cap 13 may be connected to one another using a variety of techniques including, but not limited to, adhesion and via mechanical means. For example, upper half 11 and lower half 12 may be sonically welded to one another. Alternatively, upper half 11 and lower half 12 may be corresponding molded parts that connect to one another by applying pressure along body seam 15. Similarly, filling cap 13 may be connected to upper half 11 via any of the above-described techniques.

In this desired embodiment, exemplary flow-through housing 10 may be used to form a desired device containing the above-described fluid treatment media using the following exemplary steps. Upper half 11 and lower half 12 are connected to one another to form exemplary flow-through housing 10 without filling cap 13. Exemplary flow-through housing 10 is then filled with a fluid treatment media, such as the above-described fluid treatment media comprising a support material, one or more anti-microbial components, and one or more scale inhibitors. Then, filling cap 13 is affixed to upper half 11. When fully assembled and filled, the device comprises an effective delivery device capable of delivering oligodynamic metals and/or phosphate materials into a surrounding body of fluid (e.g., water), preventing the growth of bacteria and/or the deposition of scale.

The shape of exemplary flow-through housing 10 is particularly advantageous due to the easy removal of the resulting device from containers housing a body of water, such as a humidifier tank. As can be envisioned, many humidifier tanks maintain one port for filling with water. Once the device of the present invention is dropped into a humidifier tank, since the device is of a spherical shape, the device is easily removed by tilting the humidifier tank and allowing the spherical device to drop out of the single port.

As shown in exemplary flow-through housing 10, the flow-through housing typically has one or more openings within the wall structure of the housing to allow fluid (e.g., water) into the housing. The amount of surface area occupied by the one or more openings may be described as a percent porosity. For example, a flow-through housing having a porosity of about 50% is a housing wherein 50% of the total outer surface area of the housing is covered with one or more openings. Desirably, the flow-through housing used in the present invention has a porosity of at least about 10%, more desirably at least about 20%, and even more desirably at least about 25%.

The one or more pore openings in the wall structure of the flow-through housing may have any size and shape as long as the openings prevent fluid treatment media from escaping the flow-through housing. Typically, the openings have an elongated slit shape (i.e., similar to openings 14 of exemplary flow-through housing 10), a circular shape, or a combination of both. However, it should be understood that the one or more openings may have any shape and/or size. Further, any combination of shapes and sizes may be used for multiple openings (i.e., two or more different opening may have different shapes and/or sizes in the same device).

The pore openings in the flow-through housing typically have a smallest dimension (e.g., the width for openings 14 of exemplary flow-through housing 10) that is less than about 0.6 to about 0.75 times the smallest average dimension of the enclosed fluid treatment media. In one exemplary embodiment of the present invention, each of the one or more openings in the flow-through housing has a smallest opening dimension ranging from about 10 microns to about 10,000 microns.

The interior volume of the flow-through housing may vary depending on the given application. For example, flow-through housings for use in ice making machines typically have interior volumes ranging from about 25 cubic centimeters (cc) to about 150 cc. Flow-through housings for use in applications such as humidifiers typically have interior volumes ranging from about 10 cc to about 100 cc. The size of the flow-through housing, as well as the quantity and type of fluid treatment media may be varied over a wide range. Typically, the fluid treatment media in the flow-through housing has a packing density of about 70% to about 90%.

Although not shown in FIGS. 1-2, the flow-through housing may further comprise one or more additional components integrally attached to at least one components of the flow-through housing. For example, a stem may be integrally attached to the filling cap as a separate molded part that mechanically joins to the filling cap or as a molded component of the filling cap. In this exemplary embodiment, the stem may be used to handle (e.g., grasp) the flow-through housing. Any additional components of the flow-through housing may be made from the above-described materials used to form other components of the flow-through housing.

C. Substrates

In a further exemplary embodiment, devices of the present invention comprise a substrate that may be used to support the above-described fluid treatment media. Suitable substrates include, but are not limited to, porous substrates such as papers, foams, wallboard, wallpaper, ceiling tiles, fabrics (e.g., nonwoven, woven, knitted, and mesh fabrics), and fibers (e.g., cellulosic fibers); and nonporous substrates such as films, molded polymeric substrates, glass substrates (e.g., windows), ceramic substrates, metal oxides, and metal substrates. In one desired embodiment of the present invention, the substrate comprises a paper or nonwoven fabric comprising cellulosic fibers. In a further desired embodiment of the present invention, the substrate comprises a paper or nonwoven fabric comprising cellulosic fibers alone or in combination with polymeric binder fibers, other polymeric fibers (e.g., high melting thermoplastic or thermosettable fibers), inorganic fibers (e.g., microglass fibers), or any combination thereof.

Suitable nonwoven fabrics include, but are not limited to, nonwoven fabrics formed using any conventional process such as meltblowing processes, spunbonding processes, spunlacing processes, hydroentangling processes, carding processes, needlepunching processes, papermaking processes, etc.

Suitable fibers for forming nonwoven fabrics include, but are not limited to, cellulosic fibers such as softwood pulp fibers, northern bleached softwood kraft or eucalyptus kraft pulp fibers, cotton fibers, hardwood pulp fibers, flax fibers, and wool fibers; synthetic organic fibers such as polypropylene fibers, polyethylene fibers, KEVLAR® fibers, rayon fibers, polyamide (e.g., nylon) fibers, polyester (e.g., DACRON® and DYNEL®, PET) fibers, and acrylic (OR- LON®, CRESLAN®, and ACRILAN®) fibers; synthetic inorganic fibers such as fiberglass fibers and microglass fibers; and any combination thereof.

Any combination of the above-mentioned fibers may be bonded to one another to form a paper or a nonwoven fabric using (i) mechanical bonding (e.g., hydroentangling or needlepunching), (ii) chemical bonding using a binding agent other than a fiber (e.g., using an inorganic and/or organic binding agent such as a chemical resin); (iii) thermal bonding using a polymeric binder fiber (e.g., utilizing lower melting polypropylene or polyethylene fibers to bind together other higher melting and/or cellulosic fibers); or (iv) and combination of (i) to (iii), The above-described fluid treatment media may be coated onto an outer surface and/or impregnated into a given substrate using known coating/impregnation processes resulting in a "treated substrate." Such coating/impregnation processes include, but are not limited to, dip coating, spray coating, and pad coating.

The amount of fluid treatment media applied onto and/or in a given substrate may vary depending on a number of factors including, but not limited to, the type of substrate (e.g., porous or nonporous), the type of fluid treatment media, and the fluid environment. Typically, the treated substrate comprises an effective amount of fluid treatment media in or on the substrate in an amount of up to about 10 wt % fluid treatment media based on a total weight of the treated substrate (i.e., the substrate material and the fluid treatment media). In some embodiments, such as porous substrates (e.g., papers and nonwoven fabrics), the treated substrate may comprise from about 0.3 wt % to about 10 wt % fluid treatment media based on a total weight of the treated substrate. In other embodiments, such as nonporous substrates (e.g., films), the treated substrate may comprise from about 0.3 wt % to about 10 wt % fluid treatment media based on a total weight of the treated substrate.

Treated substrates may be used in a variety of applications. For example, treated substrates may be used as "flow-through" devices in which a given fluid (potentially containing a microbial agent) flows through the treated substrate. Exemplary "flow-through" treated substrates include, but are not limited to, humidifier wicks; personal, residential, industrial, and veterinary care water filter devices and filter media; personal, residential, industrial, and medical air filters, respiratory masks and filter media. In other embodiments, treated substrates may be used as "contact" devices in which a given fluid (potentially containing a microbial agent) contacts a portion of the treated substrate, but does not flow through the treated substrate. Exemplary "contact" treated substrates include, but are not limited to, wallpaper, and other wall coverings, woven and non-woven fabrics, polymeric materials, etc.

Figure 3:
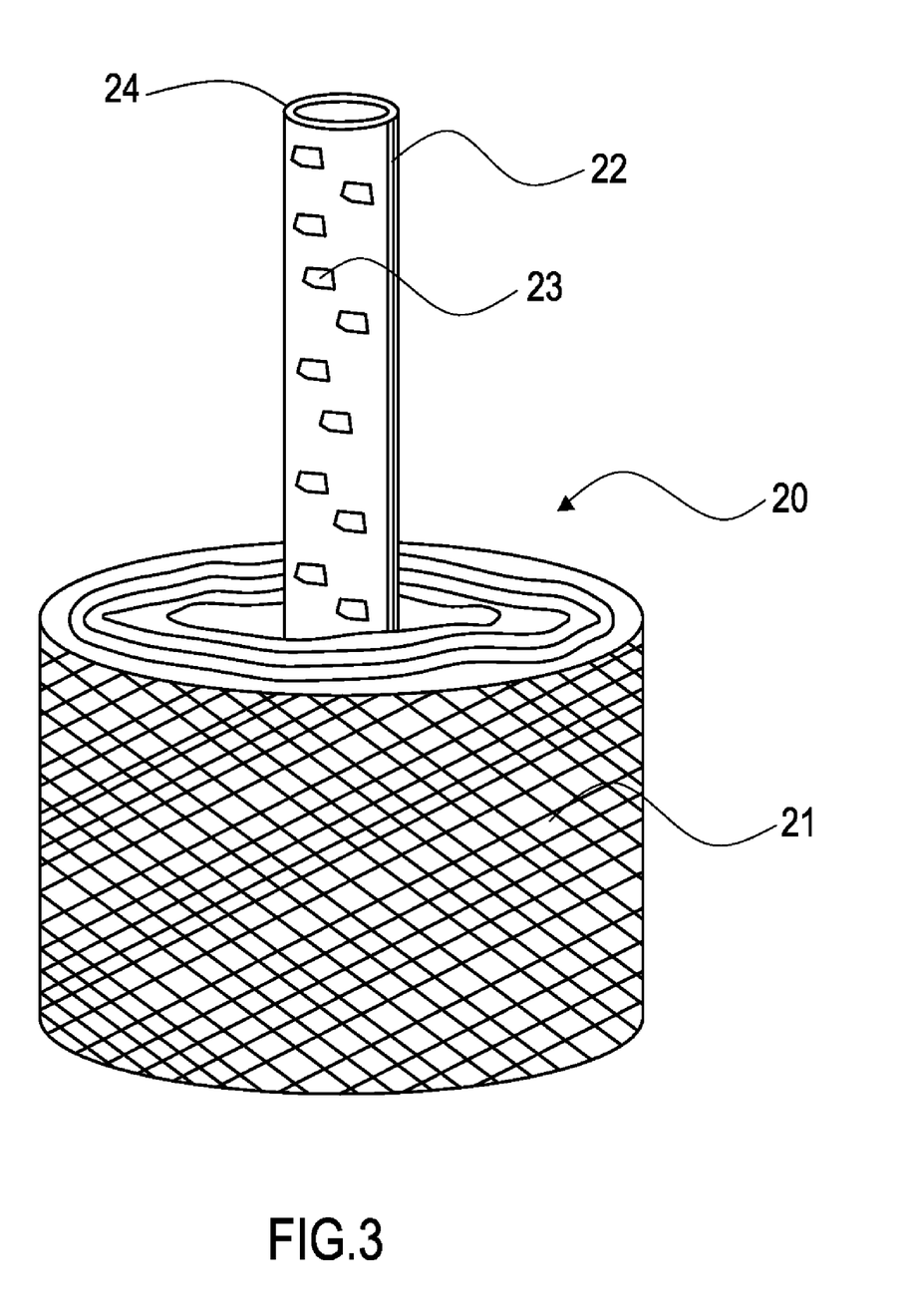
FIG. 3 depicts a perspective view of an exemplary device of the present invention comprising a treated substrate having fluid filtering and/or absorption capabilities.
Figure 4:
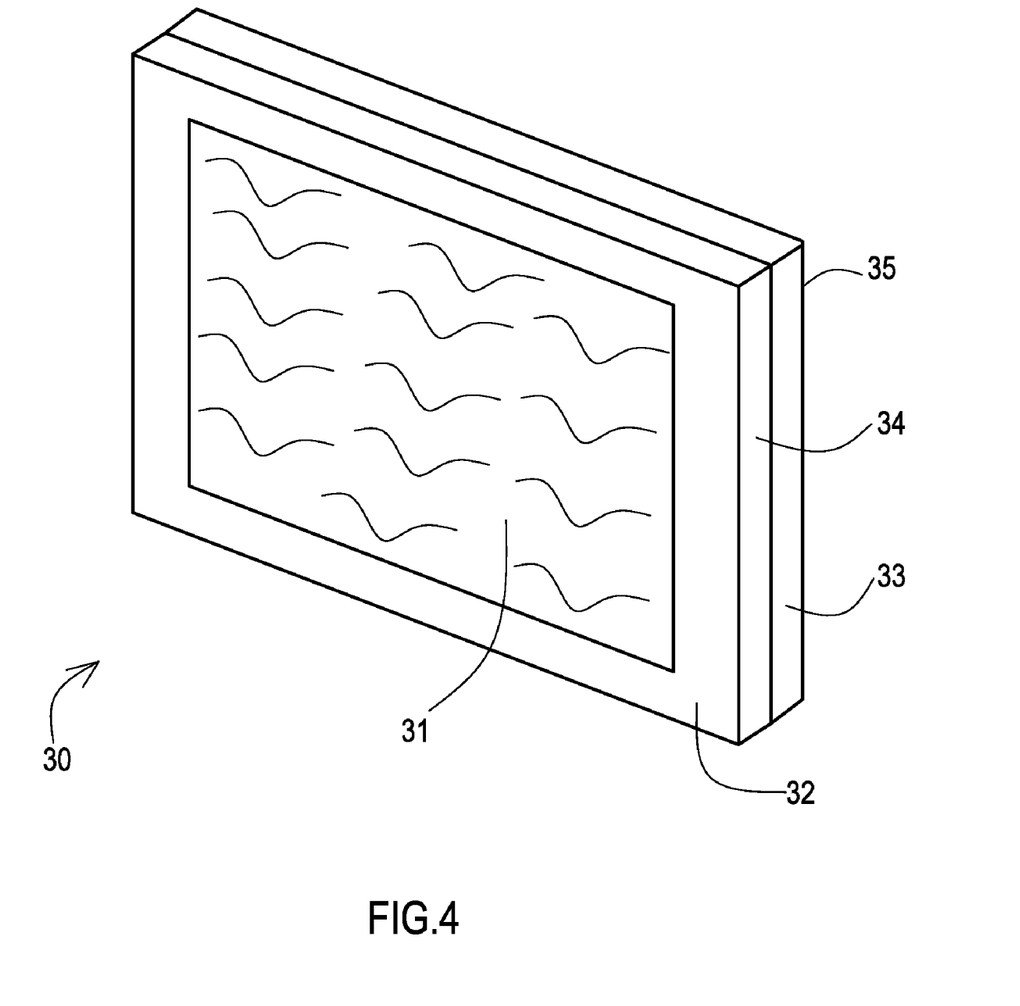
FIG. 4 depicts a perspective view of another exemplary device of the present invention comprising a treated substrate.

Exemplary treated substrates are shown in FIGS. 3-4. As shown in FIG. 3, exemplary flow-through filter 20 comprises treated substrate 21, which is positioned around a central support core 22. (Treated substrate 21 typically extends up to core end 24 so as to completely cover core 22. FIG. 3 provides a view in which a portion of treated substrate 21 has been removed to display core 22.) Core 22 can be metal, plastic, or any other material. Core 22 has perforations 23 therein to provide flow channels through filter 20 and treated substrate 21.

It should be noted that exemplary filter 20 may have any volumetric shape other than a cylindrical shape (e.g., a circular cross-sectional configuration). Suitable cross-sectional configurations other than a circular cross-sectional configuration for exemplary filter 20 include, but are not limited to, triangular, square, rectangular, oblong, oval, star, parallelogram, rhombus, hexagonal, and octagonal cross-sectional configurations. Further, the cross-sectional area through exemplary filter 20 may be substantially constant along a length of the filter or may vary along a length of the filter.

Another exemplary treated substrate of the present invention is shown in FIG. 4. In this embodiment, exemplary article 30 comprises treated substrate 31 positioned along outer surface 32 of article 30. Exemplary article 30 further comprises housing 34, which surrounds and provides support for treated substrate 31. Housing 34 may be metal, plastic or another material. Optional additional layer 33 is positioned next to housing 34, providing an outer surface 35 opposite outer surface 32. In this embodiment, treated substrate 31 may be a flow-through filter-type media or a contact substrate (e.g., wallpaper). When treated substrate 31 is a flow-through filter-type media, optional additional layer 33 may comprise, for example, another flow-through layer such as a second treated substrate similar to or different from treated substrate 31. When treated substrate 31 is a contact-type treated substrate, optional additional layer 33 may comprise, for example, an adhesive layer for attaching exemplary article 30 to a surface (e.g., the wall of a room) via outer surface 35.

It should be noted that treated substrate 31 could extend so as to cover all of outer surface 32 of article 30. Further, it should be noted that treated substrate 31 (and treated substrate 21 of FIG. 3) could comprise a single or multi-layered treated substrate comprising any of the above-mentioned substrate materials including paper or any fabric. Although not shown in FIGS. 3-4, treated substrates of the present invention and articles containing the same may have a flat or pleated configuration having any of the above-mentioned areal configurations. In other words, the treated substrates (and articles containing the same) may have a circular, triangular, square, rectangular, oblong, oval, star, parallelogram, rhombus, hexagonal, or octagonal shape. The treated substrate may have a structural support in contact with the treated substrate or may be self-supporting (i.e., the treated substrate does not require a supporting structure). Such treated substrates are particularly useful for air filtration, wherein air passes through the filter by entering a first major surface and exiting a second major surface. A non-limiting example of such a treated substrate is a rectangular, pleated filter having a length of 60 cm, a height of 30 cm, and a thickness of about 3 cm.

II. Methods of Making Fluid Treatment Devices

The present invention is further directed to methods of making the above-described compositions and devices. In one exemplary embodiment of the present invention, the method of making a fluid treatment device comprises (i) forming a flow-through housing; (ii) forming a fluid treatment media comprising (a) an anti-microbial component on (b) a support material, and (c) at least one of (i) a scale inhibitor and (ii) a disinfectant/biofilm removal material; (iii) introducing the fluid treatment media into the flow-through housing; and (iv) sealing the flow-through housing so that the fluid treatment media is contained within the flow-through housing.

In a further exemplary embodiment of the present invention, the method of making a fluid treatment device comprises (i) forming three molded parts comprising an upper half, a lower half, and a filling cap; (ii) connecting the upper half to the lower half to form a flow-through housing having a housing wall structure, a housing volume surrounded by the housing wall structure, one or more openings within the housing wall structure, and a filling cap opening; (iii) forming a fluid treatment media comprising an anti-microbial component on a support material; (iv) introducing the fluid treatment media into the filling cap opening to fill at least a portion of the housing volume with fluid treatment media; and (v) connecting the filling cap to the flow-through housing to cover the filling cap opening so that the fluid treatment media is contained within the flow-through housing. In this embodiment, the fluid treatment media may further comprise at least one of (i) a scale inhibitor and (ii) a disinfectant/biofilm removal material.

In the above-described methods of making a fluid treatment device, the resulting fluid treatment device desirably comprises a flow-through housing having a spherical shape with a diameter ranging from about 5 mm to about 500 mm. Further, the resulting fluid treatment device desirably holds from about 0.1 to about 1000 grams of the above-described fluid treatment media.

In yet a further exemplary embodiment of the present invention, the method of making a fluid treatment device comprises (i) providing a substrate; (ii) forming a fluid treatment media comprising an anti-microbial component on a support material; and (iii) applying the fluid treatment media onto the substrate so as to coat and/or impregnate the substrate with fluid treatment media. The step of applying the fluid treatment media onto the substrate may comprise any of the conventional coating processes described above (e.g., spray coating). In this embodiment, the method may further include one or more additional steps including, but not limited to, drying the treated substrate, coating the treated substrate with another coating material (e.g., an adhesive layer), laminating another layer to the treated substrate (e.g., a film having an outermost adhesive layer), assembling the treated substrate into a roll of material, and packaging the treated substrate.

In yet a further exemplary embodiment of the present invention, the method of making a fluid treatment device comprises (i) incorporating any of the above-described fluid treatment media comprising an anti-microbial component on a support material into a substrate during a substrate forming step. For example, the fluid treatment media may be incorporated into a slurry containing pulp fibers, and formed into a paper using any conventional papermaking process.

When the substrate comprises a nonwoven fabric, the nonwoven fabric may be formed using conventional processes including, but not limited to, meltblowing processes, spunbonding processes, spunlacing processes, hydroentangling processes, carding processes, needlepunching processes, papermaking processes, etc.

In the above-described methods of making a fluid treatment device, the step of forming a fluid treatment media may comprise one or more of the following steps: (i) coating and/or impregnating a support material with an anti-microbial component, (ii) optionally thermally treating the coated/impregnated support material to dry and/or cure the coating material, (iii) optionally coating and/or impregnating a support material with a bifunctional ligand, (iv) optionally coating and/or impregnating a support material having a bifunctional ligand thereon with an anti-microbial component, (v) optionally grinding and sifting solid coated/impregnated support material, solid scale inhibitor material, and/or disinfectant/biofilm removal material, when present, to obtain a desired particle size for each component, and (vi) physically blending solid coated/impregnated support material with at least one of solid scale inhibitor and solid disinfectant/biofilm removal material. An exemplary coating/impregnating step may include, but is not limited to, impregnating a suitable support material, such as alumina, with an aqueous solution of $AgNO_3$ or $Cu(NO_3)_2$ to impart oligodynamic metals in and on the surface of the support material. A further exemplary coating/impregnating step may include, but is not limited to, coating/impregnating a suitable support material, such as alumina, with an aqueous solution containing a bifunctional ligand, such as $HOCH_2CH(OH)CH_2NH_2$, and then contacting the alumina/ligand complex with an aqueous solution of $AgNO_3$ (or another soluble silver salt or complex) or $Cu(NO_3)_2$ (or another soluble copper salt or complex).

In one exemplary method of making a fluid treatment media, the method comprises the steps of (i) grinding and sifting SILIPHOS® particles (Somis Ltd.) to obtain an average particle size of about 1.0 to about 3.0 mm, and (ii) blending (a) 20 g of the SILIPHOS® particles with ($b_1$) 80 g of MB2001B (Apyron Technologies, Inc.) particles having an average particle size of about 1.0 to about 3.0 mm or ($b_2$) 80 g of AQUASTAT® XR (K2 Concepts, Inc.) particles having an average particle size of about 3.2 mm to form a substantially homogenous blend. In a further exemplary method of making a fluid treatment media, the method comprises the steps of (i) grinding and sifting SILIPHOS® particles (Somis Ltd.) to obtain an average particle size of about 1.0 to about 3.0 mm, and blending (a) 10 g of the SILIPHOS® particles with ($b_1$) 90 g of MB2001B (Apyron Technologies, Inc.) particles having an average particle size of about 1.0 to about 3.0 mm or ($b_2$) 90 g of AQUASTAT® XR (K2 Concepts, Inc.) particles having an average particle size of about 3.2 mm to form a substantially homogenous blend.

In yet a further exemplary method of making a fluid treatment media, the method comprises the steps of (i) grinding and sifting SILIPHOS® particles (Somis Ltd.) to obtain an average particle size of about 1.0 to about 3.0 mm, (ii) grinding and/or tableting ICX™ particles (A-dec Inc.) to obtain an average particle size of about 1.0 to about 3.0 mm, and (iii) blending (a) 10 g of the SILIPHOS® particles with ($b_1$) 90 g of MB2001B (Apyron Technologies, Inc.) particles having an average particle size of about 1.0 to about 3.0 mm or ($b_2$) 90 g of AQUASTAT® XR (K2 Concepts, Inc.) particles having an average particle size of about 3.2 mm, and (c) 10 g of the ICX™ particles having an average particle size of about 1.0 to about 3.0 mm to form a substantially homogenous blend.

III. Methods of Using Fluid Treatment Devices

The present invention is even further directed to methods of using the above-described fluid treatment devices. In one exemplary embodiment of the present invention, the method comprises a method of treating a body of water in a container, wherein the method comprises the step of inputting a fluid treatment device into the body of water within the container, wherein the fluid treatment device comprises (i) a flow-through housing having a housing wall structure, a housing volume surrounded by the housing wall structure, and one or more openings within the housing wall structure; and (ii) fluid treatment media occupying at least a portion of the housing volume within the flow-through housing, wherein the fluid treatment media comprises (a) an anti-microbial component on (b) a support material, and optionally (c) at least one of (c)(i) a bifunctional ligand, (c)(ii) a scale inhibitor and (c)(iii) a disinfectant/biofilm removal material; wherein the fluid treatment media has a size that prevents the water treatment media from escaping the one or more openings within the housing wall structure.

In a further exemplary embodiment of the present invention, the method of treating a body of water in a container comprises the step of (I) inputting a fluid treatment device into the body of water within the container, wherein the fluid treatment device comprises (i) a flow-through housing having a housing wall structure, a housing volume surrounded by the housing wall structure, and one or more openings within the housing wall structure, wherein the housing wall structure of the flow-through housing comprises an upper half, a lower half connected to the upper half, and a filling cap connected to the upper half or the lower half, and the one or more openings are positioned within the upper half, the lower half, or both; and (ii) fluid treatment media occupying at least a portion of the housing volume within the flow-through housing, wherein the fluid treatment media comprises (a) an anti-microbial component on (b) a support material; wherein the fluid treatment media has a size that prevents the fluid treatment media from escaping the one or more openings within the housing wall structure. In this embodiment, the fluid treatment media may further comprise at least one of (i) a bifunctional ligand, (ii) a scale inhibitor and (iii) a disinfectant/biofilm removal material.

The fluid treatment devices may be used to treat bodies of water in a variety of containers. For example, the fluid treatment devices of the present invention may be used to treat bodies of water in room humidifiers, vaporizers, ice machines, drinking water coolers, cooling towers, medical air humidifiers, medical oxygen humidifiers, hot and cold water therapy spas, CPAP machines, dental water lines, drinking water storage tanks, hiking and military canteens, industrial boilers, any vessel capable of containing at least a portion of a plant, cut flowers, a fruit or vegetable (e.g., vases, aquariums, pots, pans, storage or shipping container, etc.), as well as other drinking water or non-drinking water storage tanks.

The fluid treatment devices of the present invention may also be used to extend the life and/or vitality of a plant, such as cut flowers, fruits or vegetables. In one exemplary embodiment, the method of extending the life of a plant comprises (a) inputting at least a portion of a plant into a body of water within a container; and (b) inputting a fluid treatment device into the body of water, wherein the fluid treatment device comprises (i) a flow-through housing having a housing wall structure, a housing volume surrounded by the housing wall structure, and one or more openings within the housing wall structure, and (ii) fluid treatment media occupying at least a portion of the housing volume within the flow-through housing, wherein the fluid treatment media comprises an anti-microbial component on a support material, and the fluid treatment media has a size that prevents the fluid treatment media from escaping the one or more openings within the housing wall structure. The fluid treatment media may comprise an anti-microbial component on a support material alone or in combination with one or more of (i) a bifunctional ligand, (ii) a scale inhibitor and (iii) a disinfectant/biofilm removal material such as those described above.

In this embodiment, the fluid treatment devices of the present invention may be used to extend the life and/or vitality of a variety of plants, fruits or vegetables including, but not limited to, cut flowers, such as roses; other decorative flowers or plant parts such as gladiolus, carnations, gerbera, or alstroemeria; potted plants; vegetables, such as cabbage or lettuce; and fruits, such as cherries or oranges. In one exemplary embodiment of extending the life of cut roses, the fluid treatment device comprises fluid treatment media comprising a blend of (a) 20 g of SILIPHOS® particles having an average particle size of about 1.0 to about 3.0 mm, and either ($b_1$) 80 g of MB2001B (Apyron Technologies, Inc.) particles having an average particle size of about 1.0 to about 3.0 mm or ($b_2$) 80 g of AQUASTAT® XR (K2 Concepts, Inc.) particles having an average particle size of about 3.2 mm.

In a further exemplary embodiment of the present invention, the method comprises a method of treating a body of air, wherein the method comprises the step of positioning a fluid treatment device in an area so that air contacts and/or flows through the fluid treatment device, wherein the fluid treatment device comprises (i) a substrate; and (ii) fluid treatment media positioned on and/or in the substrate, wherein the fluid treatment media comprises (a) an anti-microbial component on (b) a support material, and optionally (c) one of (i) a bifunctional ligand, (ii) a scale inhibitor and (iii) a disinfectant/biofilm removal material.

Other potential applications include, but are not limited to, the use of the disclosed treated substrates as wipes (e.g., baby wipes), bandages and wound dressings, geotextiles (e.g., soil stabilizing fabrics, etc.), isolation gowns, surgical gowns, surgical drapes and covers, surgical scrub suits, surgical masks and caps, carpeting and upholstery, packaging—to sterilize medical products, and table cover laminates.

The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Preparation of a Fluid Treatment Media

An exemplary fluid treatment media was prepared as follows. 100 g of alumina particles having an average particle size of about 3.0 mm were immersed in an aqueous solution containing 1.0 M $AgNO_3$. The alumina particles were removed from the aqueous solution after soaking for about 1 minute, and then dried in an oven at a drying temperature of about 600° C. The resulting particles were suitable for use as a fluid treatment media.

Example 2

Preparation of a Fluid Treatment Media

An exemplary fluid treatment media was prepared as follows. SILIPHOS® particles (BK Giulini Chemie Gmbh & Co.) were ground and sifted to obtain particles having an average particle size of about 3.0 mm. 20 g of the ground SILIPHOS® particles were blended with 80 g of the fluid treatment media formed in Example 1. The resulting mixture was suitable for use as a fluid treatment media.

Example 3

Preparation of a Fluid Treatment Device Comprising a Flow-Through Housing

An exemplary fluid treatment device was prepared as follows. A flow-through housing substantially similar to exemplary housing 10 of FIG. 1 and having a spherical shape and an outer diameter of about 33 mm diameter was formed from three (3) separate pieces of injection molded polystyrene. The three separate pieces consisted of an upper half (substantially similar to upper half 11 of exemplary housing 10 of FIG. 1), a lower half (substantially similar to lower half 12 of exemplary housing 10 of FIG. 1), and a filling cap (substantially similar to filling cap 13 of exemplary housing 10 of FIG. 1).

The upper half and the lower half of the flow-through housing were sonically welded together. 10 g of the fluid treatment media formed in Example 1 was poured into the flow-through housing. The filling cap was then sonically welded onto the upper half to enclose the fluid treatment media.

The resulting fluid treatment device was placed in a room humidifier containing about 4.5 liters of water. The water within the room humidifier was substantially free of microbes for a period of 30 days.

Example 4

Preparation of a Fluid Treatment Device Comprising a Flow-Through Housing

An exemplary fluid treatment device was prepared using the procedure as outlined in Example 3 above except that alternative fluid treatment media was used in place of the fluid treatment media formed in Example 1. Sample devices were prepared as shown in Table 1 below.

TABLE 1

Sample Devices and Fluid Treatment Media Contained Therein

| Sample | Fluid Treatment Media Composition | Amount |
|---|---|---|
| 1 | fluid treatment media of Example 2 | 10.0 g |
| 2 | a homogenous blend of (i) 10 wt % of SILIPHOS ® particles (BK Giulini Chemie Gmbh & Co.) having an average particle size of about 1.0 mm, and (ii) 90 wt % of AQUASTAT ® XR (K2 Concepts, Inc.) particles having an average particle size of about 3.2 mm | 10.0 g |
| 3 | a homogenous blend of (i) 20 wt % of SILIPHOS ® particles (BK Giulini Chemie Gmbh & Co.) having an average particle size of about 1.0 mm, and (ii) 80 wt % of AQUASTAT ® XR (K2 Concepts, Inc.) particles having an average particle size of about 3.2 mm | 20.0 g |
| 4 | a homogenous blend of (i) 50 wt % of SILIPHOS ® particles (BK Giulini Chemie Gmbh & Co.) having an average particle size of about 1.0 mm, and (ii) 50 wt % of AQUASTAT ® XR (K2 Concepts, Inc.) particles having an average particle size of about 3.2 mm | 200 g |
| 5 | a homogenous blend of (i) 90 wt % of SILIPHOS ® particles (BK Giulini Chemie Gmbh & Co.) having an average particle size of about 1.0 mm, and (ii) 100 wt % of AQUASTAT ® XR (K2 Concepts, Inc.) particles having an average particle size of about 3.2 mm | 200 g |
| 6 | a homogenous blend of (i) 20 wt % of SILIPHOS ® particles (BK Giulini Chemie Gmbh & Co.) having an average particle size of about 1.0 mm, and (ii) 80 wt % of AQUASTAT ® XR (K2 Concepts, Inc.) particles having an average particle size of about 3.2 mm | 2,000 g |

The resulting fluid treatment devices were used in a variety of water-containing apparatus. For example, sample device 1 was placed into a room humidifier containing about 4.5 liters of water. The water within the room humidifier was substantially free of microbes for a period of 30 days. Further, sample device 2 was placed into a room vaporizer containing about 4.5 liters of water. The water within the room vaporizer was substantially free of microbes for a period of 30 days.

Example 5

Use of a Fluid Treatment Device to Extend the Life and/or Vitality of Cut Flowers A dozen roses having an average stem length of about 30.5 cm (12 in) were split into two groups. Six roses were placed in a vase containing tap water (control sample 1), while the other six roses were placed in a vase containing the same tap water plus an exemplary fluid treatment device prepared as described in Example 3 above (test sample 7).

After two weeks, the roses in test sample 7 still looked new, while the roses in control sample 1 died in less than 7 days.

Example 6

Preparation of a Fluid Treatment Media

An exemplary fluid treatment media was prepared as follows. ICX™ particles (A-dec Inc.) were ground and sifted to obtain particles having an average particle size of about 3.0 mm. 20 g of the ground ICX™ particles were blended with 80 g of the fluid treatment media formed in Example 1. The resulting mixture was suitable for use as a fluid treatment media.

Example 7

Preparation of a Fluid Treatment Device Comprising a Flow-Through Housing

An exemplary fluid treatment device was prepared using the procedure as outlined in Example 3 above except that the fluid treatment media formed in Example 6 was poured into the flow-through housing. The resulting exemplary fluid treatment device was used to treat water in a room humidifier containing about 4.5 liters of water. The water within the room humidifier was substantially free of microbes for a period of 30 days.

Example 8

Preparation of a Fluid Treatment Media

An exemplary fluid treatment media was prepared as follows. 100 g of alumina particles having an average particle size of about 3.0 mm were immersed in an aqueous solution containing $HOOCCH_2CH_2NH_2$. The alumina particles were removed from the aqueous solution after soaking for about 1 minute, and then dried in an oven at a drying temperature of about 100° C. The particles were then immersed in an aqueous solution containing $AgNO_3$. The alumina particles were removed from the second aqueous solution after soaking for about 1 minute, and then dried in an oven at a drying temperature of about 100° C. The resulting particles were suitable for use as a fluid treatment media.

Example 9

Preparation of a Fluid Treatment Device

An exemplary fluid treatment device was prepared as follows. An aqueous solution or suspension was prepared by adding 250 grams of AQUASTAT® XR (WC Grade) (K2 Concepts, Inc.) particles having an average particle size of less than about 10 μm to a solution containing 20 grams of CARBOPOL® 940 (Noveon, Inc., Cleveland, Ohio) in 500 ml. of distilled water. The mixture was blended for 35 minutes.

A HEPA grade paper commercially available under the trade designation HIPERM PLUS™ from Hollingsworth & Vose Company (East Walpole, Mass.) and having an initial basis weight of 36.3 $g/m^2$ was coated using the aqueous solution by dipping the paper into the aqueous solution. The coated paper was then dried at 66° C. (150° F.) for 2 hours. The resulting coated paper had a coating weight of about 40 $g/m^2$.

Example 10

Preparation of a Fluid Treatment Device

The process of Example 9 was repeated by coating an autogeneously spunbonded nylon nonwoven fabric commercially available under the trade designation CEREX® from Cerex Advanced Fabrics, Inc. (Cantonment, Fla.). The uncoated fabric had an initial basis weight of 94 $g/m^2$. The resulting coated fabric had a coating weight of about 100 $g/m^2$.

Example 11

Preparation of a Fluid Treatment Device

An exemplary fluid treatment device was prepared using a conventional papermaking process in which the aqueous solution of Example 9 was incorporated into a pulp slurry. The resulting paper had a weight percent of anti-microbial material of about 3.0 wt % based on a total weight of the paper.

Example 12

Preparation of a Fluid Treatment Device

An exemplary fluid treatment device was prepared using a conventional papermaking process in which the aqueous solution or suspension of Example 9 was incorporated into a pulp slurry comprising the following fibers: 27 wt % mercerized softwood pulp, 5 wt % cotton fibers (composed of linter pulp, "rag" pulp or staple cotton), and 68 wt % northern bleached softwood kraft. The resulting paper had a weight percent of anti-microbial material of about 3.0 wt % based on a total weight of the paper.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A fluid treatment device for controlling microbial growth in air or potable water systems, said device comprising:
   a porous substrate selected from paper, foam, wallboard, wallpaper, ceiling tile, fabric, or fibers; and
   fluid treatment media (i) on an outer surface of the porous substrate, (ii) within the porous substrate, or (iii) both (i) and (ii), said fluid treatment media comprising a physical mixture of:
   a first set of particles or beads comprising an anti-microbial component coating on a support material with the anti-microbial component coating comprising one or more coating layers on said support material, said anti-microbial component comprising a transition metal, a transition metal oxide, a transition metal salt, or a combination thereof; and
   a second set of particles or beads comprising a scale inhibitor comprising an inorganic phosphate, a phosphonate, a polycarboxylate, or a combination thereof.

2. The device of claim 1, wherein the transition metal is selected from the group consisting of Sc, Ti, Sn, V, Cr, Mn, Fe, Co, Ni, Cu, Zn, Y, Zr, Nb, Mo, Tc, Ru, Rh, Pd, Ag, Cd, Hf, Ta, W, Re, Os, Ir, Pt, Au, Hg, Rf, Db, Sg, Bh, Hs, Mt, Uun, Uuu, Uub, and combinations thereof.

3. The device of claim 2, wherein the support material is selected from the group consisting of activated carbon, alumina, silica, titanium oxide, tin oxide, lanthanum oxide, copper oxide, vanadium oxide, manganese oxide, nickel oxide, iron oxide, zinc oxide, zirconium oxide, magnesium oxide, thorium oxide, polyethylene, polypropylene, polyvinylchloride, polystyrene and polyethylene terephthalate.

4. The device of claim 3, wherein the support material is selected from the group consisting of alumina and polyethylene terephthalate.

5. The device of claim 4, wherein the transition metal is selected from the group consisting of Ag, Cu, Zn, and combinations thereof.

6. The device of claim 5, wherein the transition metal is Ag and the support material is alumina.

7. The device of claim 6, wherein said second set of particles or beads comprise an inorganic phosphate.

8. The device of claim 1, wherein said fluid treatment media comprises a physical mixture of (i) said first set of particles or beads, (ii) said second set of particles or beads, and (iii) a third set of particles or beads comprising at least one disinfectant/biofilm removal material comprising sodium percarbonate.

9. The device of claim 1, wherein said porous substrate comprises paper, a woven fabric or a nonwoven fabric.

10. The device of claim 9, wherein said porous substrate comprises a nonwoven fabric comprising cellulosic fibers.

11. A fluid treatment device for controlling microbial growth in air or potable water systems, said device comprising:
   a porous sheet-like substrate having opposite first and second major surfaces and an outer edge extending (i)

around an outer periphery of said porous sheet-like substrate and (ii) separating said opposite first and second major surfaces from one another; and fluid treatment media (i) on an outer surface of the porous sheet-like substrate, (ii) within the porous sheet-like substrate, or (iii) both (i) and (ii), said fluid treatment media comprising:

a first set of particles or beads comprising an anti-microbial component coating on a particulate support material with the anti-microbial component coating comprising one or more coating layers on said particulate support material, said anti-microbial component comprising a transition metal, a transition metal oxide, a transition metal salt, or a combination thereof;

wherein at least a portion of each of said first and second major surfaces is exposed, and each of said opposite first and second major surfaces is free of an adhesive coating.

12. The device of claim 11, wherein the transition metal is Ag and the particulate support material is alumina.

13. The device of claim 11, wherein said fluid treatment media further comprises a second set of particles or beads comprising a scale inhibitor comprising an inorganic phosphate, a phosphonate, a polycarboxylate, or a combination thereof.

14. The device of claim 13, wherein said second set of particles or beads comprise polyphosphate glass particles.

15. The device of claim 11, wherein said porous sheet-like substrate comprises a nonwoven fabric comprising cellulosic fibers.

16. The device of claim 15, wherein said nonwoven fabric further comprises microglass fibers.

17. The device of claim 16, wherein said nonwoven fabric further comprises an inorganic or organic binder material.

18. A fluid treatment device for controlling microbial growth in air or potable water systems, said device comprising:

a porous substrate comprising paper or a nonwoven substrate; and fluid treatment media (i) on an outer surface of the porous substrate, (ii) within the porous substrate, or (iii) both (i) and (ii), said fluid treatment media comprising a physical mixture of:

a first set of particles or beads comprising an anti-microbial component coating on a support material with the anti-microbial component coating comprising one or more coating layers on said support material, said anti-microbial component comprising silver and said support material comprising alumina; and a second set of particles or beads comprising a scale inhibitor comprising an inorganic glassy polyphosphate.

19. The device of claim 18, wherein said paper or nonwoven substrate comprises cellulosic fibers.

20. The device of claim 18, wherein said device has a flow-through construction so that a fluid may flow through said device by entering a first major outer surface of said paper or nonwoven substrate and exiting a second major outer surface of said paper or nonwoven substrate opposite the first major outer surface.

* * * * *